United States Patent [19]
Santori et al.

[11] Patent Number: 4,894,179
[45] Date of Patent: Jan. 16, 1990

[54] ABSORBENT COMPOSITION CONTAINING A TERTIARY AMINO AZABICYCLIC ALCOHOL AND AN AMINE SALT

[75] Inventors: Guido Santori; W. S. Winston Ho, both of Annandale; Eugene L. Stogryn, Edison, all of N.J.

[73] Assignee: Exxon Research and Engineering Company, Florham Park, N.J.

[21] Appl. No.: 106,797

[22] Filed: Oct. 13, 1987

[51] Int. Cl.⁴ .............................................. C09K 3/00
[52] U.S. Cl. .................................. 252/189; 252/190; 252/191
[58] Field of Search ........................ 252/189, 190, 191

[56] References Cited

U.S. PATENT DOCUMENTS

| | | | |
|---|---|---|---|
| 2,722,500 | 11/1955 | Rippie et al. | 208/289 |
| 2,946,652 | 7/1960 | Bloch | 423/229 |
| 3,139,324 | 6/1964 | Housset | 423/229 |
| 3,535,260 | 10/1970 | Singh | 252/189 |
| 3,653,810 | 4/1972 | Bratzler et al. | 423/226 |
| 3,848,057 | 11/1974 | Leder et al. | 423/223 |
| 4,080,423 | 3/1978 | Smith et al. | 423/226 |
| 4,112,052 | 9/1978 | Sartori et al. | 423/228 |
| 4,153,674 | 5/1979 | Verloop et al. | 423/573 R |
| 4,240,922 | 12/1980 | Sartori et al. | 252/189 |
| 4,336,233 | 6/1982 | Appl et al. | 423/228 |
| 4,405,580 | 9/1983 | Stogryn et al. | 423/226 |
| 4,405,581 | 9/1983 | Savage et al. | 423/226 |
| 4,405,582 | 9/1983 | Stogryn et al. | 423/228 |
| 4,405,583 | 9/1983 | Stogryn et al. | 423/228 |
| 4,405,585 | 9/1983 | Sartori et al. | 423/228 |
| 4,471,138 | 9/1984 | Stogryn | 564/508 |
| 4,487,967 | 12/1984 | Stogryn et al. | 564/474 |
| 4,525,294 | 6/1985 | Sartori et al. | 252/182 |
| 4,578,517 | 3/1986 | Johnson et al. | 564/479 |
| 4,618,481 | 10/1986 | Heinzelmann et al. | 423/228 |
| 4,665,195 | 5/1987 | Stogryn et al. | 548/523 |

FOREIGN PATENT DOCUMENTS 0134948 3/1985 European Pat. Off. .
2017524 10/1979 United Kingdom .

OTHER PUBLICATIONS

Delos F. DeTar, "Effects of Alkyl Groups on Rates of Acyl-Transfer Reactions", J. Org. Chem, 1980, 45, 5166–5174.
Delos F. DeTar, "Effects of Alkyl groups on Rates of $S_n2$ Reactions", J. Org. Chem, 1980, 45, 5174–5176.

Primary Examiner—Alan L. Rotman
Assistant Examiner—Catherine S. Kolby Scalzo
Attorney, Agent, or Firm—Ronald D. Hantman

[57] ABSTRACT

A new alkaline absorbent solution containing a tertiary amino azabicyclic alcohol in combination with its salt with a strong acid and/or in combination with a severely-hindered aminoacid is provided. A process for the removal of $H_2S$ from fluid mixtures using this absorbent solution to produce a very low level of $H_2S$ in the treated fluid is also provided. The process is also suitable for the selective removal of $H_2S$ from fluid mixtures comprising $H_2S$ and $CO_2$. Use of the above absorbent solution leads to higher selectivity for $H_2S$ without damaging capacity than observed when the tertiary amino azabicyclic alcohol is used alone without additive.

10 Claims, 3 Drawing Sheets

ABSORBENT COMPOSITION CONTAINING A TERTIARY AMINO AZABICYCLIC ALCOHOL AND AN AMINE SALT

FIELD OF THE INVENTION

This invention relates to an absorbent composition and a process for the selective removal of hydrogen sulfide from a hydrogen sulfide-containing gas using the absorbent composition.

BACKGROUND

Processes for the selective absorption of $H_2S$ from gaseous mixtures utilizing alkaline liquid absorbents containing amino compounds are known. In particular, U.S. Pat. No. 4,405,580 discloses the use of a tertiary amino azabicyclic alcohol, such as tropine.

Although the alkaline absorbents containing the amino compounds are capable of removing acidic gases such as hydrogen sulfide from hydrogen sulfide-containing gaseous mixture, it is progressively more difficult particularly at low pressures to remove hydrogen sulfide at normal operating conditions to a level such that the absorbent-treated gaseous mixture (i.e., exit gas) contains less than about 10 volume parts per million (vppm) hydrogen sulfide. When it is desired to produce a gas having less than 10 vppm hydrogen sulfide, the treated gas, for example, a Claus tail gas, containing more than 10 vppm hydrogen sulfide is typically incinerated to convert the remaining hydrogen to $SO_2$. Therefore, it would be advantageous to improve the efficiency of the known alkaline amine absorbents to increase the amount of hydrogen sulfide that they are capable of removing at normal operating conditions so as to yield a treated gas having less than about 10 vppm, preferably less than 1 vppm, hydrogen sulfide.

J. H. Dibble's European Patent Application No. 84107586.4 (Publication No. 013948) published Mar. 27, 1985 discloses that the absorption of hydrogen sulfide at low pressures by certain alkaline absorbents, which may contain an alkanolamine, is enhanced by using in the absorbent an acid or an acid forming material having a pKa of 6 or less in an amount sufficient to protonate less than 22% of the alkaline material to produce a treated gas having less than 10 vppm hydrogen sulfide.

U.S. Pat. No. 4,618,481 issued Oct. 21, 1986 to Exxon Research and Engineering Company discloses the absorption of hydrogen sulfide by the use of an alkaline absorbent composition comprising a severely hindered amine and an amine salt to produce a treated gas having less than 10 vppm hydrogen sulfide.

U.S. Pat. No. 4,153,674 discloses the addition of strong acidic compounds such as acids and ammonium salts thereof to aqueous alkanolamine absorbent solutions, see column 6, lines 33 to 48.

U.S. Pat. No. 2,722,500 discloses removing acid gases from hydrocarbon gases by using an alkanolamine salt of a polybasic acid having a high ionization constant, for example, phosphoric acid, and hydrochloric acid. It discloses that it is convenient to react the acid in advance with the amine.

U.S. Pat. No. 3,139,324 discloses an absorbent solution for $H_2S$ comprising an ethanolamine and a polybasic acid such as phosphoric acid. The ethanolamine is present in an amount between 0.20 gram mole and 0.02 gram mole per liter.

U.S. Pat. No. 3,848,057 discloses an absorbent solution comprising ethanolamine and a basic salt. The acid gases may containing $H_2S$ and $SO_2$.

U.S. Pat. No. 4,080,423 discloses a process for absorbing acidic gases using a basic component and a weakly dissociated compound such as a weak acid or a salt thereof. Acids and salts listed as suitable include phosphoric acid and sulfurous acid. As shown in Example 1, the basic component may be ethanolamine and the salt can be sodium phosphate, and the acid gas to be purified may comprise $H_2S$ and $SO_2$.

It now has been found that a treated gas having less than 10 vppm $H_2S$ can be obtained from a low pressure gas and that in treating fluids comprising $H_2S$ as well as $CO_2$, an increasing $H_2S$ selectivity can be achieved by utilizing an absorbent composition comprising a tertiary amino azabicyclic alcohol in combination with its salt with a strong acid or in combination with a severely-hindered aminoacid.

SUMMARY OF THE INVENTION

The present invention is a new alkaline absorbent solution containing a tertiary amino azabicyclic alcohol in combination with its salt with a strong acid and/or in combination with a severely-hindered aminoacid. Another aspect of the present invention is the use of the above solution for the selective removal of $H_2S$ from gaseous streams down to levels of 10 vppm or lower. Use of the above solution leads to higher selectivity for $H_2S$ than observed when the tertiary amino azabicyclic alcohol is used alone without the additives.

DETAILED DESCRIPTION OF THE INVENTION

Figure 1:
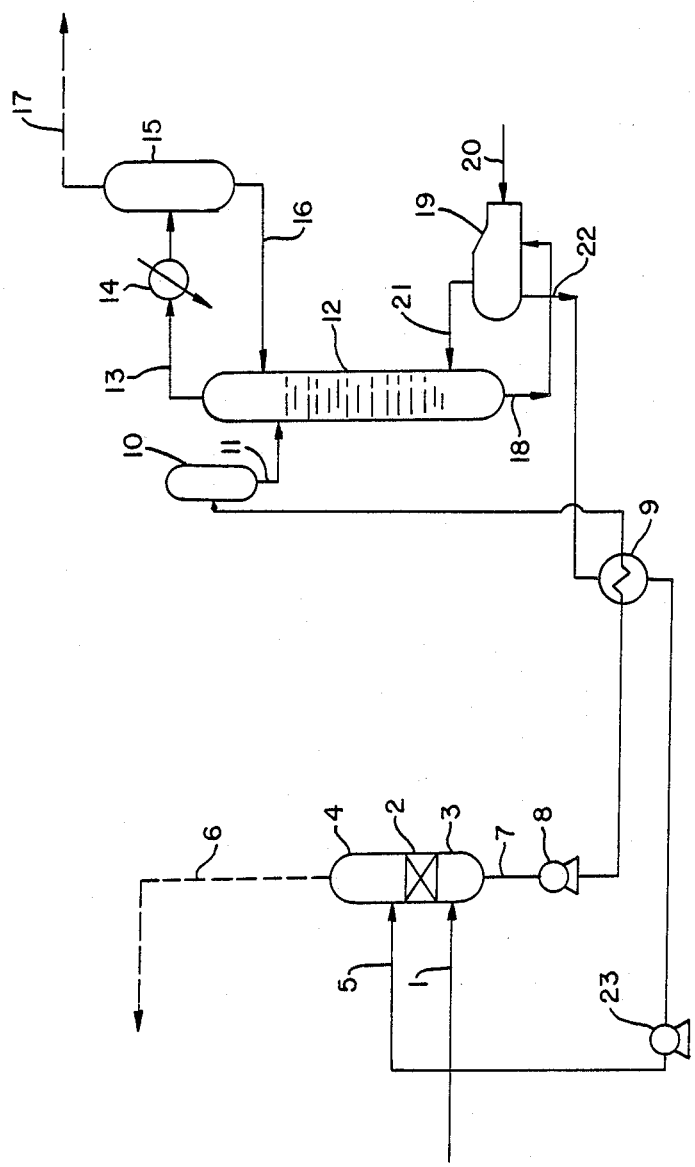
FIG. 1 is a diagrammatic flow sheet illustrating an absorption-regeneration unit for selective removal of $H_2S$ from gaseous streams containing $H_2S$ and $CO_2$.

The new absorbent solution of the present invention containing a tertiary amino azabicyclic compound in combination with its salt with a strong acid and/or in combination with a severely-hindered aminoacid can reduce the $H_2S$ level in the treated gas to below 10 vppm. Thus, this makes unnecessary the use of an incinerator or a Stretford unit downstream from the amine scrubber.

The tertiary aminoazabicyclic alcohols herein are compounds wherein the two fused rings, which share at least one side, each have 4–10 ring atoms, preferably 4–7 ring atoms, of which one ring atom is nitrogen. Each ring may be unsubstituted or substituted, and the nitrogen atom forming the tertiary amino portion of the compound is situated within the bicyclic framework at a bridgehead or non-bridgehead ring position. The hydroxyl group(s) of the alcohol may be directly connected to the ring and/or may be connected to a hydrocarbon chain, preferably containing 2–10 carbon atoms, arranged in a linear or branched fashion and connected to the heterocycle via a ring nitrogen or a ring carbon atom. It is noted that the hydrocarbon chain may be alkoxylated, i.e., may contain one or more ether oxygen atoms, in the case where the hydroxyl group is attached to a hydrocarbon chain, it may be primary or secondary.

Representatives of such azabicyclic alcohols include, for example, tropine, pseudotropine, 9-methylgranatanin-3-ol, isoquinuclidine ethanol, trachelanthamidine, 4-hydroxymethyl-quinuclidine, N-hydroxyethylnortropine, N-hydroxyethyl(9-azabicyclo[3.3.1]nonane), N-hydroxyethoxyethyl(9-azabicyclo[4.2.1]nonane), 3-hydroxymethyl-8-methyl-8-azabicyclo[3.2.1]octane, and the like. The amine salt suitable for use as component of the absorbent of the present invention is the reaction product of (a) a tertiary amino azabicyclic alcohol and (b) a strong acid, or a thermally decomposable salt of a strong acid, i.e., ammonium salt, or a component capable of forming a strong acid, and mixtures thereof.

The acid or thermally decomposable salt, such as the ammonium salt, or an acid forming component, used as reactant to form the amine salts with the above-described tertiary aminoazabicyclic alcohols is a strong acid having at least one of the pKa of not more than about 7, preferably a pKa of not more than 6, more preferably a pKa of less than 5. The term "pKa" with reference to the acid is used herein to designate the logarithm of the reciprocal of the ionization constant of the acid measured at 25° C. When the acid is a polybasic acid, and therefore, has several ionization constants, at least one of the pKa must be not more than 7. Ionization constants are given in Lange's *Handbook of Chemistry* published by Handbook Publishers, Sandusky, Ohio, 1952, pages 1229–1235. The component reacted with the azabicyclic compound to form the amine salt may be a strong acid, a salt of a strong acid, the cation of which will decompose, such as ammonium salts of strong acids, or a precursor of strong acid. Suitable strong acids include inorganic acids such as sulfuric acid, sulfurous acid, phosphoric acid, phosphorous acid, pyrophosphoric acid; organic acids such as acetic acid, formic acid, adipic acid, benzoic acid, etc. Suitable salts of these acids include the ammonium salts, for example, ammonium sulfate, ammonium sulfite, ammonium phosphate and mixtures thereof. Preferably, sulfuric acid, ammonium sulfate (a salt) or $SO_2$ (a precursor of the acid) is used as reactant. Suitable salts are those that are non-volatile at conditions used to regenerate the absorbent composition.

A sufficient amount of amine salt is present in the initial fresh or regenerated absorbent composition to provide at least about a mole ratio of 0.2:1 of amine salt to tertiary aminoazabicyclic alcohol, preferably a mole ratio ranging from about 0.2:1 to 4:1, more preferably about 0.2:1 to 1:1, most preferably from about 0.3:1 to 1:1 of amine salt per mole of said alcohol.

A sufficient amount of a severely hindered aminoacid is present in the initial fresh or regenerated absorbent composition to provide at least about a mole ratio of 0.01:1 of said aminoacid to tertiary aminoazabicyclic alcohol, preferably a mole ratio ranging from about 0.1:1 to 4:1, more preferably from about 0.2:1 to 1:1, most preferably from about 0.3:1 to 1:1 of said aminoacid per mole of said alcohol.

Examples on sterically-hindered aminoacids are N-tertiarybutylalanine and N-tertiarybutylglycine.

The amine and additive for the present invention are dissolved in a liquid medium. In a fresh or regenerated initial absorbent composition comprising water, the unreacted amine may be present, for example, in an amount ranging from 5 to 70 wt%, the additive may be present in an amount ranging from about 5 to 40 wt%, calculated as the tertiary aminoazabicyclic alcohol, the balance being water and all said weights being based on the weight of the total liquid absorbent composition.

The liquid medium in which amine and additive are contained prior to use may be water, an organic solvent and mixtures thereof. Preferably, the liquid medium comprises water.

Suitable organic solvents include physical absorbents (as opposed to chemical absorbents) such as those described in U.S. Pat. No. 4,112,051, the teachings of which are hereby incorporated by reference and may be, for example, aliphatic acid amides, N-alkylated pyrrolidones, sulfones, sulfoxides, glycols and the mono- and di-ethers thereof. The preferred physical absorbents are sulfones, preferably sulfolane. If a mixture of solvent and water is used as the liquid medium, a typical amount of solvent may range from 0.1 to 5 moles per liter of total absorbent composition, preferably from about 0.5 to 3 moles per liter, depending upon the particular components used.

The absorbent composition of the present invention may include a wide range of additives typically employed in selective gas removal processes, such as antifoaming agents, antioxidants, corrosion inhibitors and the like in an effective amount.

Three characteristics which are of ultimate importance in determining the effectiveness of the amine absorbent solutions herein for $H_2S$ removal are "selectivity", "loading" and "capacity". The term "selectivity" as used throughout the specification is defined as the following mole ratio fraction:

$$\frac{\text{(moles of } H_2S/\text{moles of } CO_2 \text{) in liquid phase}}{\text{(moles of } H_2S/\text{moles of } CO_2 \text{) in gaseous phase}}$$

The higher this fraction, the greater is the selectivity of the absorbent solution for the $H_2S$ in the gas mixture.

By the term "loading" is meant the concentration of the $H_2S$ gas physically dissolved and chemically combined in the absorbent solution as expressed in weight percent of the solution. The best solutions are those which exhibit good selectively up to a relatively high loading level. The solutions used in the practice of the present invention typically have a "selectivity" of not substantially less than 10 at a "loading" of 0.2 wt% $H_2S$, preferably, a selectivity of not substantially less than 10 at a loading of 0.4 wt% $H_2S$ or more.

"Capacity" is defined as the moles or weight percent of $H_2S$ loaded in the absorbent solution at the end of the absorption step minus the moles or weight percent of $H_2S$ loaded in the absorbent solution at the end of the desorption step. High capacity enables one to reduce the amount of amine solution to be circulated and use less heat or steam during regeneration.

The acid gas mixture herein necessarily includes $H_2S$, and may optionally include other gases such as $CO_2$, $H_2$, CO, $N_2$, COS, HCN, $CS_2$, $C_2H_4$, $NH_3$, and the like. Often such gas mixtures are found in combustion gases, refinery gases, town gas, natural gas, syn gas, water gas, propane, propylene, heavy hydrocarbon gases, etc. The absorbent solution herein is particularly effective when the gaseous mixture is a gas, obtained, for example from shale oil retort gas, coal or gasification of heavy oil with air/steam or oxygen/steam, thermal conversion of heavy residual oil to lower molecular weight liquids and gases, or in sulfur plant tail gas clean-up operations.

The absorption step of this invention generally involves contacting the gaseous stream with the absorbent solution in any suitable contacting vessel. In such processes, the normally gaseous mixture containing $H_2S$ and $CO_2$ from which the $H_2S$ is to be selectively removed may be brought into the intimate contact with the absorbant solution using conventional means such as a tower or vessel packed with, for example, rings or with sieve plates, or a bubble reactor.

In a typical mode of practicing the invention, the absorption step is conducted by feeding the normally gaseous mixture into the lower portion of the absorption tower while fresh absorbent solution is fed into the upper region of the tower. The normally gaseous mixture, freed largely from the $H_2S$, emerges from the upper portion of the tower, and the loaded absorbent solution, which contains the selectively absorbed $H_2S$, leaves the tower near or at its bottom. Preferably, the inlet temperature of the absorbent solution during the absorption step is in the range of from about 20° to about 100° C., and more preferably from 40° to about 60° C. Pressures may vary widely; acceptable pressures are between 5 and 2000 psia, preferably 20 to 1500 psia, and most preferably 25 to 1000 psia in the absorber. The contacting takes place under conditions such that the $H_2S$ is selectively absorbed by the solution. The absorption conditions and apparatus are designed so as to minimize the residence time of the liquid in the absorber to reduce $CO_2$ pickup while at the same time maintaining sufficient residence time of gas mixture with liquid to absorb a maximum amount of $H_2S$ gas. The amount of liquid required to be circulated to obtain a given degree of $H_2S$ removal will depend on the chemical structure and basicity of the amino compound and on the partial pressure of $H_2S$ in the feed gas. Gas mixtures with low partial pressures such as those encountered in thermal conversion processes will require less liquid under the same absorption conditions than gases with higher partial pressures such as shale oil retort gases.

A typical procedure for the selective $H_2S$ removal phase of the process comprises selectively absorbing $H_2S$ via countercurrent contact of the gaseous mixture containing $H_2S$ and $CO_2$ with the aqueous solution of the absorbent composition in a column containing a plurality of trays at a low temperature, e.g., below 45° C., and at a gas velocity of at least about 0.3 ft/sec (based on "active" or aerated tray surface), depending on the operating pressure of the gas, said tray column having fewer than 20 contact trays with, e.g., 4–16 trays being typically employed.

After contacting the normally gaseous mixture with the absorbent solution, which becomes saturated or partially saturated with $H_2S$, the solution may be at least partially regenerated so that it may be recycled back to the absorber. As with absorption, the regeneration may take place in a single liquid phase. Regeneration or desorption of the acid gases from the absorbent solution may be accomplished by conventional means such as pressure reduction of the solution or increase of temperature to a point at which the absorbed $H_2S$ flashes off, or by passing the solution into a vessel of similar construction to that used in the absorption step, at the upper portion of the vessel, and passing an inert gas such as air or nitrogen or preferably steam upwardly through the vessel. The temperature of the solution during the regeneration step should be in the range from about 50° to about 170° C., and preferably from about 80° to 120° C., and the pressure of the solution on regeneration should range from about 0.5 to about 100 psia, preferably 1 to about 50 psia. The absorbent solution, after being cleansed of at least portion of the $H_2S$ gas, may be recycled back to the absorbing vessel. Makeup absorbent may be added as needed.

In the preferred regeneration techniques, the $H_2S$-rich solution is sent to the regenerator wherein the absorbed components are stripped by the steam which is generated by re-boiling the solution. Pressure in the flash drum and stripper is usually 1 to about 50 psia, preferably 1 to about 30 psia, and the temperature is typically in the range from about 50° to 170° C., preferably 80° to 120° C. Stripper and flash temperatures will, of course, depend on stripper pressure; thus at about 1 to 30 psia stripper pressures, the temperature will be about 80° to about 120° C. during desorption. Heating of the solution to be regenerated may very suitably be effected by means of indirect heating with low-pressure steam. It is also possible, however, to use direct injection steam.

In one embodiment for practicing the entire process herein, as illustrated in FIG. 1, the gas mixture to be purified is introduced through line 1 into the lower portion of a gas-liquid countercurrent contacting column 2, said contacting column having a lower section 3 and an upper section 4. The upper and lower sections may be segregated by one or a plurality of packed beds as desired. The absorbent solution as described above is introduced into the upper portion of the column through a pipe 5. The solution flowing to the bottom of the column encounters the gas flowing countercurrently and dissolves the $H_2S$ preferentially. The gas freed from most of the $H_2S$ exits through a pipe 6 for final use. The solution, containing mainly $H_2S$ and some $CO_2$, flows toward the bottom portion of the column from which it is discharged through pipe 7. The solution is then pumped via optional pump 8 through an optional heat exchanger and cooler 9 disposed in pipe 7, which allows the hot solution from the regenerator 12 to exchange heat with the cooler solution from the absorber column 2 for energy conservation. The solution is entered via pipe 7 to a flash drum 10 equipped with a line (not shown) which vents to line 13 and then introduced by pipe 11 into the upper portion of the regenerator 12, which is equipped with several plates and effects the desorption of the $H_2S$ and $CO_2$ gases carried along in the solution. This acid gas mixture is passed through a pipe 13 into a condenser 14 wherein cooling and condensation of water and amine solution from the gas occur. The gas then enters into a separator 15 where further condensation is effected. The condensed solution is returned through pipe 16 to the upper portion of the regenerator 12. The gas remaining from the condensation, which contains $H_2S$ and some $CO_2$, is removed through pipe 17 for final disposal, e.g., to a vent or incinerator or an apparatus which converts the $H_2S$ to sulfur, such as a Claus unit or a Stetford conversion unit (not shown).

The solution is liberated from most of the gas which it contains while flowing downward through the regenerator 12 and exits through pipe 18 at the bottom of the regenerator for transfer to a reboiler 19. Reboiler 19, equipped with an external source of heat (e.g., steam injected through pipe 20), vaporizes a portion of this solution (mainly water) to drive further $H_2S$ therefrom. The $H_2S$ and steam driven off are returned via pipe 21 to the lower section of the regenerator 12 and exited through pipe 13 for entry into the condensation stages of gas treatment. The solution remaining in the reboiler 19 is drawn through pipe 22, cooled in heat exchanger 9, and introduced via the action of pump 23 (optional if pressure is sufficiently high) through pipe 5 into the absorber column 2).

The invention is illustrated further by the following examples which, however, are not to be taken as limiting in any respect. All parts and percentages, unless expressly stated to be otherwise, are by weight.

EXAMPLE 1

This example shows that addition of tropine sulfate to tropine lowers the lean loading without affecting the rich loading.

The reaction apparatus was a 500-ml flask, equipped with reflux condenser, thermometer, magnetic bar and three-way stopcock. 150 g of water and 50 g of tropine, corresponding to 0.355 moles, were put into the flask. The solution was 1.77 molar. From the top of the reflux condenser vacuum was applied until the solution began to boil. Then $H_2S$ was admitted into the flask from a plastic bag. When absorption stopped, a sample was taken and found to contain 5.99% $H_2S$, corresponding to a loading of 1.06 moles of $H_2S$ per mole of tropine.

The solution was refluxed for 3 hours, then a sample of lean solution was taken and found to contain 0.272% of $H_2S$, which corresponded to 0.045 mole of $H_2S$ per mole of tropine.

The experiment was repeated, using the following solution:
67.74 g of tropine
6.10 of $H_2SO_4$
126.16 g of $H_2O$ The total weight was again 200 g. The concentration of free tropine was the same as before, i.e., 1.77 molar. The concentration of tropine.$(H_2SO_4)_{0.5}$ was 0.63 molar. The absorption-desorption experiment was carried out as before. The rich loading was 1.02 moles of $H_2S$ per mole of tropine, i.e., practically identical to the rich loading obtained without additive. The lean loading was 0.011 moles of $H_2S$ per mole of tropine, i.e., definitely lower than that obtained without the additive.

EXAMPLE 2

Selective $H_2S$ Removal from a Mixture Containing $H_2S$ and $CO_2$

Figure 2:
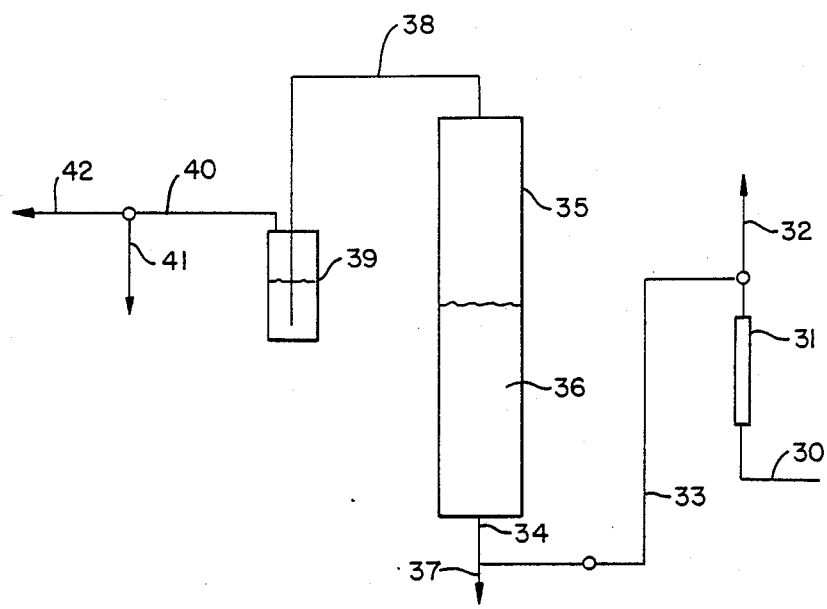
FIG. 2 is a diagrammatic flow sheet illustrating an experimental sparged absorber unit for use in rapid determination of the selectivity of the absorbent composition for selective removal of $H_2S$ from gaseous streams containing $H_2S$ and $CO_2$.

FIG. 2 illustrates the sparged absorber unit, operated on a semibatch mode, used to evaluate the selectivity for $H_2S$ removal of the amine absorbent solutions of the invention herein. A gas mixture comprised of 10% $CO_2$, 1% $H_2S$ and 89% $N_2$ expressed in the volume percent, respectively, was passed from a gas cylinder (not shown) through line 30 to a meter 31 measuring the rate at which the gas is fed to the absorber. For all examples this rate was 3.6 liters per minute. The gas was then passed through line 32 to a gas chromatography column (not shown) continuously monitoring the composition of the inlet gas and through lines 33 and 34 to a sparged absorbent unit 35 which is a cylindrical glass tube 45 cm high and 3.1 cm in diameter charged with 100 ml of the absorbent amine solution 36. The gas was passed through the solution at a solution temperature of 36° C., and about 5-ml samples of the solution were periodically removed from the bottom of the absorber unit through lines 34 and 37 to be analyzed for $H_2S$ and $CO_2$ content. The $H_2S$ content in the liquid sample was determined by titration with silver nitrate. The $CO_2$ content of the liquid sample was then analyzed by acidifying the sample with an aqueous solution of 10% HCl and measuring the evolved $CO_2$ by weight gain on NaOH-coated asbestos.

While the solution was being periodically withdrawn from the bottom of the absorber unit, the gas mixture was removed from the top thereof via line 38 to a trap 39 which served to scrub out any $H_2S$ in the outlet gas. The resulting gas could optionally then be passed via lines 40 and 41 for final disposal or via line 42 to a gas chromatography column (not shown) for periodic evaluation of the composition of the outlet gas to check for system leaks. For purposes of the examples, the $H_2S$ and $CO_2$ contents of the inlet gas phase were measured and the $H_2S$ and $CO_2$ contents of the liquid phase were determined as described above. These data were used to calculate selectivity values of the amine absorbent solution as defined above, which were plotted as a function of the loading of the absorbent solution containing $H_2S$ and $CO_2$ in units of weight percent of $H_2S$ in the solution.

Figure 3:
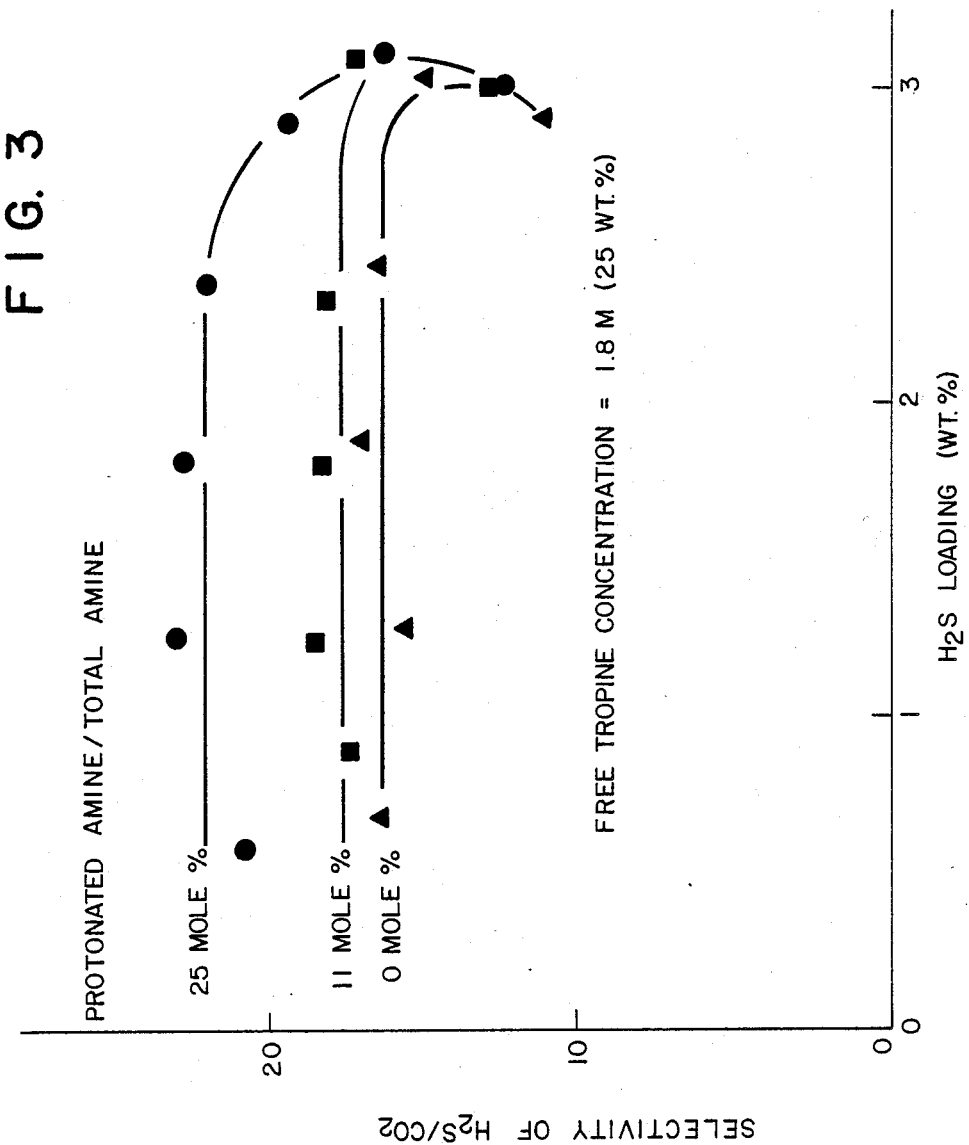
FIG. 3 shows that adding tropine sulfate to tropine leads to an increase in selectivity for $H_2S$.

Experiments were carried out at a constant free tropine concentration of 1.8 M, corresponding to 25 wt%. An experiment was carried out without additive, two more after adding tropine.$(H_2SO_4)_{0.5}$ so as to have ratios of protonated amine to total amine of 0.11 and 0.25, respectively. The attached FIG. 3 shows the results. Addition of tropine.$(H_2SO_4)_{0.5}$ increased selectivity for $H_2S$ without damaging capacity as compared with the experiment without additive.

What is claimed is:

1. A composition comprising: (1) at least one tertiary amino azabicyclic alcohol and (2) an amine salt, said amine salt being the reaction product of said azabicyclic alcohol and a component selected from the group consisting of an acid having at least one pKa of not more than about 7, a decomposable salt of an acid having at least one pKa of not more than about 7, a compound capable of forming an acid having a pKa of not more than about 7 and a mixtures thereof, said amine salt and said tertiary azabicyclic alcohol being present in said composition in a mole ratio of said amine salt to said tertiary amino azabicyclic alcohol of at least about 0.2:1 to 4:1.

2. The composition of claim 1 wherein said composition additionally comprises a liquid selected from the group consisting of water, an organic solvent and mixtures thereof.

3. The composition of claim 1 wherein said azabicyclic alcohol is selected from the group consisting of tropine, pseudotropine, 9-methylgranatanin-3-ol, isoquinuclidine ethanol, trachelanthamidine, 4-hydroxymethyl-quinuclidine, N-hydroxyethyllnortropine, N-hydroxyethyl (9-azabicyclo [3.3.1]nonane), N-hydroxyethoxyethyl(9-azabicyclo[4.2.1]nonane), and 3-hydroxymethyl-8-methyl-8-azabicyclo[3.2.1]octane.

4. The composition of claim 1 wherein said component reacted with said alcohol is selected from the group consisting of sulfuric acid, phosphoric acid, phosphorous acid, pyrophosphoric acid, sulfurous acid, and mixtures thereof.

5. The composition of claim 1 wherein said component reacted with said alcohol is selected from the group consisting of ammonium sulfate, ammonium sulfite, sulfur dioxide, ammonium phosphate and mixtures thereof.

6. The composition of claim 1 wherein said mole ratio of said amine salt to said alcohol ranges from about 0.2:1 to 1:1.

7. The composition of claim 1 wherein said mole ratio of said amine salt to said alcohol ranges from about 0.3:1 to 1:1.

8. The composition of claim 1 wherein said composition comprises water and wherein said amine salt is a non-volatile water soluble amine salt.

9. The composition of claim 1 wherein said composition comprises from about 5 to 70 wt. % of said alcohol, from about 5 to 40 weight percent of said amine salt calculated as said alcohol, and the balance being water.

10. The composition of claim 1 wherein said amine salt is the reaction product of tropine and $H_2SO_4$.

* * * * *